United States Patent
Lake et al.

(10) Patent No.: US 9,327,423 B2
(45) Date of Patent: May 3, 2016

(54) WOOD PRESERVATIVES AND METHODS FOR TREATING WOOD

(71) Applicant: Liquid Lignin Company, LLC, Easley, SC (US)

(72) Inventors: Michael A. Lake, Mt. Pleasant, SC (US); Craig R. McIntyre, Dayton, MT (US); Philip L. Robinson, Isle of Palms, SC (US)

(73) Assignee: LIQUID LIGNIN COMPANY, LLC, Easley, SC (US)

( * ) Notice: Subject to any disclaimer, the term of this patent is extended or adjusted under 35 U.S.C. 154(b) by 0 days.

(21) Appl. No.: 14/149,113

(22) Filed: Jan. 7, 2014

(65) Prior Publication Data
US 2015/0189870 A1 Jul. 9, 2015

(51) Int. Cl.
*B27K 3/08* (2006.01)
*A01N 59/14* (2006.01)
*B27K 3/15* (2006.01)
*B27K 3/16* (2006.01)
*B27K 3/34* (2006.01)
*B27K 3/50* (2006.01)
*B27K 3/52* (2006.01)

(52) U.S. Cl.
CPC . *B27K 3/08* (2013.01); *A01N 59/14* (2013.01); *B27K 3/153* (2013.01); *B27K 3/163* (2013.01); *B27K 3/34* (2013.01); *B27K 3/50* (2013.01); *B27K 3/52* (2013.01); *Y10T 428/31989* (2015.04)

(58) Field of Classification Search
CPC ........ A01N 25/24; B27K 3/0278; B27K 3/08; B27K 3/15; B27K 3/153; B27K 3/163; B27K 3/34; B27K 3/50; B32B 27/10; Y10T 428/31989
USPC .......................................... 428/532; 427/393
See application file for complete search history.

(56) References Cited

U.S. PATENT DOCUMENTS

| 2,194,827 | A | | 3/1940 | Gordon |
| 4,007,004 | A | * | 2/1977 | Bailey et al. ..................... 8/636 |
| 4,929,454 | A | | 5/1990 | Findlay et al. |
| 5,087,457 | A | | 2/1992 | Bryant et al. |
| 5,207,823 | A | | 5/1993 | Shiozawa |
| 6,146,766 | A | | 11/2000 | Slimak et al. |
| 6,508,869 | B2 | | 1/2003 | Tseng et al. |
| 6,896,908 | B2 | | 5/2005 | Lloyd et al. |
| 2007/0087213 | A1 | | 4/2007 | Robinson et al. |
| 2008/0063884 | A1 | * | 3/2008 | Robinson et al. ............. 428/541 |
| 2011/0294991 | A1 | * | 12/2011 | Lake et al. .................... 530/500 |
| 2012/0161916 | A1 | * | 6/2012 | Eng et al. ...................... 336/212 |
| 2012/0201947 | A1 | * | 8/2012 | Stuart .......................... 426/635 |

FOREIGN PATENT DOCUMENTS

| WO | 9527600 A | 10/1995 |
| WO | 2012161916 A2 | 11/2012 |

OTHER PUBLICATIONS

Notification or Trasmittal of The International Search Report and The Written Opinion of the International Searching Authority, or The Declartion, issued in International Application No. PCT/US2015/010142 dated Apr. 1, 2015; 18 pages.

* cited by examiner

*Primary Examiner* — Leszek Kiliman
(74) *Attorney, Agent, or Firm* — Cantor Colburn LLP

(57) ABSTRACT

Treated wood, wood preservative compositions, and methods for treating wood generally include applying to the wood a wood preservative composition comprising a boron containing compound and a pH-reduced black liquor comprising soluble lignin, wherein the boron-containing compound is soluble in the pH-reduced black liquor and wherein the pH-reduced black liquor is derived from a carbonation process or an acid addition process of black liquor having phase-separated solid lignin and/or dense liquid lignin removed therefrom, and drying the wood.

31 Claims, No Drawings

WOOD PRESERVATIVES AND METHODS FOR TREATING WOOD

BACKGROUND

The present disclosure generally relates to wood preservatives and methods of treating wood. More particularly, the wood preservatives and methods of treating wood include applying to the wood a composition including a boron-containing compound and carbonated black liquor subsequent to removal of at least a portion of the lignin in the black liquor.

Chromated copper arsenate (CCA), a leach-resistant wood preservative known for exterior application, has been removed from the commercial market voluntarily by its manufacturers in 2003 because of the toxic nature of arsenic and chromium. Since then, there has been a continuing effort to develop suitable alternative systems. A number of alternative, non-arsenical pesticidal treatments containing heavy metals (primarily copper) have been proposed. For example, U.S. Pat. No. 4,929,454 teaches the treatment of wood with a mixture of a copper compound and a quaternary ammonium compound. This technology has been commercialized under the name ammoniated copper quaternary amine (ACQ). ACQ has excellent insect resistance, but it is considerable more costly than CCA, and it has a tendency to promote the growth of white mold on the wood surface. Furthermore, ACQ-treated wood may exhibit corrosion problems with most metal fasteners when the treated wood is placed into service. Special fasteners having high corrosive resistance is required for the ACQ treated-wood, causing an additional cost of using ACQ-treated wood for construction. The industry has since moved to corrosion resistant fasteners such as stainless steel or plastic coatings. Furthermore, there has been increasing concerns on the toxicity and environmental impact of wood preservative containing heavy metals.

Borate has been used as wood preservative for more than 50 years, since it is effective against most wood destroying organisms such as fungi, termite and wood-boring beetles. Furthermore, borate has a low acute mammalian toxicity and low environmental impact. Borate has been considered as an excellent candidate for the CCA replacement for wood preservative application. However, the well-known disadvantage of borate wood preservative is that borate is readily soluble in water, and easily leaches out of the treated wood upon contact with water. As a result, the use of borate preservative is limited to the treated wood for interior applications.

Several methods have been used to prevent the leaching of impregnated borate preservative from the treated wood. U.S. Pat. No. 2,194,827 uses solubilized metal such as zinc and copper to fix borate in wood. This method requires high concentration of ammonia to solubilize such metals and borates, resulting in excessive ammonia volatility and noxious fumes that is undesirable for large scale preparation. U.S. Pat. No. 6,896,908 addresses the ammonia off-gas issue by dissolving a high concentration of copper and/or zinc metal fixative agent in an aqueous solution of ammonia, volatile organic acid and ammonium salts. The combination of a volatile organic acid and ammonia provides a high rate of metal dissolution without requiring excessive levels of ammonia in solution, and the ammonium salt reduces the level of free ammonia needed for dissolution of metals. U.S. Pat. No. 5,207,823 discloses copper borate and/or zinc borate in combination of amine as a leach-resistant borate wood preservative. PCT Patent No. 95/27,600 teaches the use of nitrite to improve fixation of preservatives in wood, when the preservatives contains one or more copper and/or zinc salts of weak acid, and optionally boric acid and quaternary ammonium salt. U.S. Pat. No. 6,146,766 discloses the use of water soluble sodium silicate/borax mixture wherein the impregnated silicate component can be polymerized to reduce its water-solubility, thereby decreasing the leaching rate of water-soluble preservative from the treated wood. U.S. Pat. No. 6,508,869 uses amine oxide to improve leaching resistance of boron preservatives from the treated wood. In U.S. Pat. No. 5,087,457, polyammonium salts formed through the reaction of diamine and dihalide, are used in combination with borate to reduce leaching rate. However, the problem with these methods is that even the most water-insoluble borates, boric esters, and borate complexes will, on prolonged contact with water, hydrolyze to form boric acid which will leach out of the wood.

Therefore, a need exists for improved preservatives and methods for treating wood that overcomes the problems noted above.

BRIEF SUMMARY

Disclosed herein are treated wood products, wood preservative compositions and methods of applying the wood preservative composition.

The wood preservative composition comprises a boron containing compound; and a pH-reduced black liquor comprising soluble lignin, wherein the boron containing compound is soluble in the pH-reduced black liquor and wherein the pH-reduced black liquor is derived from a carbonation process and/or an acid addition process of black liquor having phase separated solid lignin and/or dense liquid lignin removed therefrom.

The treated wood comprises wood; at least one boron-containing component, and pH-reduced black liquor comprising soluble lignin, wherein the boron containing compound is soluble in the pH-reduced black liquor and wherein the pH-reduced black liquor is derived from a carbonation process and/or an acid addition process of black liquor having phase-separated solid lignin and/or dense liquid lignin removed therefrom.

The method for treating wood, comprises applying to the wood, a wood preservative formulation comprising a boron containing compound, and pH-reduced black liquor comprising soluble lignin, wherein the boron containing compound is soluble in the pH-reduced black liquor and wherein the pH-reduced black liquor is derived from a carbonation process or an acid addition process of black liquor having phase-separated solid lignin and/or dense liquid lignin removed therefrom.

In another embodiment, the method for treating wood comprises applying a boron containing compound to the wood; and applying a pH-reduced black liquor to the wood, wherein the pH-reduced black liquor comprises soluble lignin, wherein the boron containing compound is soluble in the pH-reduced black liquor, and wherein the pH-reduced black liquor is derived from a carbonation process or an acid addition process of black liquor having phase-separated solid lignin and/or dense liquid lignin removed therefrom.

The disclosure may be understood more readily by reference to the following detailed description of the various features of the disclosure and the examples included therein.

DETAILED DESCRIPTION

Disclosed herein are wood preservative compositions and methods for treating wood that generally include applying to the wood a mixture including a boron containing compound and black liquor at a pH of about 13 to about 9-10 that is obtained after phase-separation and removal of at least a portion of the lignin contained therein. In one embodiment, the black liquor is carbonated black liquor having a pH less than 13 to about 9-10 after carbonation and any phase-separated lignin solid or dense liquid lignin therein is removed. The carbonated black liquor, also referred to herein as CBL, functions as a wood protectorant that impedes the leaching of borates and the like from wood when exposed to water such as may occur during rain. As a result, the preservative properties of the boron containing compound are maintained in the treated wood.

Alternatively, the pH-reduced black liquor is obtained by acid addition. Any acid can be used to achieve pH reduction of black liquor from a pH of about 13 to 14 to a pH of about 9 to 10. Suitable acids include, without limitation, $H_2SO_4$, acetic acid, formic acid, and the like. Less preferred are those acids generally not desired within host mills such as hydrochloric acid, nitric acid, and the like. However, some host mills have developed processes and capabilities that make these amenable for acid addition.

The pH-reduced black liquor with at least a portion of the lignin removed can be obtained from the black liquor stream produced within pulp and paper mills, such as from the kraft pulping process. As used herein, the term "black liquor" is the spent cooking liquor produced during pulping when digesting pulpwood into paper pulp and is typically removed from the host paper mill's recovery system downstream of an efficiently-performing soap separator, since tall oil impurities are considered deleterious to the operation of the unit operations of the process and the downstream applications. The black liquor typically has an initial pH of about 13 to 14 and is generally an aqueous solution of lignin residues, hemicellulose, and the inorganic chemicals used in the pulping process. The lignin residues are generally classified as one of two types: the Klason lignin (KL) which are those lignin components insoluble at pH 3 or above and the acid-soluble lignin which have components soluble at pH 3 or below. About 60-80% of the KL residues contained with the black liquor can be phase-separated by carbonation of and/or acid addition to the black liquor, which effectively reduces the pH to about 9-10. Once the phase-separated solid lignin precipitates and/or dense liquid-lignin phase are removed, the leftover solution is isolated and is referred to hereinafter as the pH-reduced black liquor. Consequently, the pH-reduced black liquor (i.e., carbonated black liquor CBL) contains components that are soluble at the resulting pH of the pH-reduction process, which includes soluble lignin, soluble organic acids, and various water soluble salts. In some embodiments, the pH-reduction process and resulting pH decrease is decremental so as to fractionate (i.e., phase-separate) a selected portion of the lignin residue based on molecular weight and/or structure such as is disclosed in U.S. application Ser. No. 14/066,985 entitled "pH-Induced Fractionation Processes for Recovery of Lignin", filed on Oct. 30, 2013 incorporated herein by reference in its entirety. As used herein, the term "dense liquid-lignin phase" generally refers to the denser phase that phase separates from a less dense (top) phase of the black liquor during the pH-reduction process. The dense liquid-lignin phase may then be further acidified where it becomes a solid, and then washed to provide a solid lignin product. In some pH-reduction processes, the lignin phase separates as a solid from the carbonated black liquor solution.

As noted above, the CBL after the carbonation process and/or the acid reduced black liquor can have a pH as low as about 9-10, which can then be used directly to form the wood preservative composition by mixing with a boron containing compound. The boron containing compound is selected to be soluble at the pH of the pH-reduced black liquor solution so as to form a homogeneous solution that can be readily applied and impregnate the wood product to be treated. Generally, depending on the amount of carbonation or acid addition, the pH of the pH-reduced black liquor will range from about 12-13 to about 9-10. Upon additional acidification, the lignin that was soluble within the pH-reduced black liquor after the pH-reduction process can be made to precipitate and/or form solid-phase lignin. This is an important attribute since the inner matrix of most wood that is to be treated typically has a pH of about 5. Consequently, the lignin and some of the other soluble compounds within the pH-reduced black liquor will precipitate along with the boron containing compound upon application to the wood product. While generally not instantaneous, the precipitated lignin fractions reduce leaching of the boron containing compound from the wood matrix upon exposure to the environment. Using boric acid salts as an example, the lignin and other components acidified within the wood matrix forms ionic complexes with the boric acid salts. These ionic complexes have a markedly reduced diffusion rate from the wood matrix relative to simple salts of boric acid without the lignin present. An example of a boric acid salt is disodium octoborate tetrahydrate (DOT), which is a popular wood preservative for interior applications but is generally not used for exterior applications because of its high diffusion rate when exposed to water, e.g., rain. In contrast, the diffusion rate of the corresponding ionic complex with lignin is much lower, which reduces the propensity for leaching and renders it much more suitable for outdoor applications.

Optionally, prior to or subsequent to formulation of the pH-reduced black liquor with the boron containing compound, the formulation thereof may be subjected to a membrane filtration process to remove salts and low molecular weight lignin as well as other low molecular components such as organic acids, and the like. The membrane is selected to permit the lower molecular weight lignins, carboxylic acids, and salts to pass through the membrane as a permeate, which can then be mixed with the boric acid salt such as DOT to serve as a borate protectorant.

The molecular weight (MW) of the lignin fractions is what generally determines its solubility. Lignins that precipitate at pH 10 and lower generally have molecular weights generally near or lower than 2000 Daltons. Some of these lignin fragments are actually the base monomers the trees use to build the lignin molecule in nature, such as syringyl, conniferyl, and cinnamyl alcohols. This permeate can be further refined in a second membrane separation, where the membrane is sufficiently designed to allow inorganic salt compounds to pass as permeate, with the retentate containing the compounds which are effective as borate protectorants, such as low molecular weight lignins, organic acids, and hemicellulose compounds. The sodium and sulfur salts, which are of value to the host papermaking operation, can then be returned to the host mill which makes sodium hydroxide and sodium sulfide in their chemical recovery operations. In this manner, the retentate of this second membrane separation has very low value to the papermaker, since the valuable KL for fuel and sodium and sulfur inorganics are removed. The separation and recovery of these low molecular weight lignin, acids and/or salts may further reduce leaching of the boron containing compounds from the wood matrix once applied, since they have been concentrated using the aforementioned membrane separations.

Membranes could be used to separate the same fractions from black liquor, but in this case, the membrane's lifetime is negatively impacted by the high pH of the black liquor. Lowering the pH from about 13 to 14 to about 9 to 10 allows much more variety in the selection of membranes that can be used and increases the lifetime of those expensive membranes. Also, by first removing the KL fraction, the fouling of membranes from lignin precipitation is reduced significantly. Accordingly, membrane separation can be used to isolate these medium molecular weight (MW) lignin fractions, with MWs generally between about 200 to about 2000 Daltons, which is more commercially attractive for this application of impeding the leaching of borates in treated wood. Organic acids and hemicellulose fractions with similar MW ranges are also concentrated in this fashion. While not wanting to be bound by theory, it is believed that this "soup" of components is effective as protectorants, inhibiting the leaching of borates.

In still another embodiment, the pH-reduced black liquor is further treated to reduce odor. For example, the pH-reduced black liquor may be subjected to an oxygenation process to oxidize common odorous compounds resulting from the Kraft pulping process including, but not limited to mercaptans (e.g., methyl mercaptan, and the like), sulfides (e.g., dimethyl sulfide, dimethyl disulfide, and the like), and the like. Suitable oxygenation processes include reaction with an oxidant such as hydrogen peroxide. Alternatively, the pH-reduced black liquor may be subjected to a high-shear cavitation process to violently mix with oxygen such as using the ShockWave Power™ Reactor commercially available from HydroDynamics, Inc. Membrane separation, as discussed above may also be used, independently or in combination, with the oxygenation process. By itself, membrane filtration can be used to remove at least a portion of the odorous compounds.

Similarly, the color of the pH-reduced black liquor may be reduced using conventional means such as by feeding the pH-reduced black liquor through activated charcoal bed, reaction with hydrogen peroxide, exposure to actinic radiation, or the like.

Wood that is suitable for use in the present disclosure may be of any species suitable for construction. Preferred woods include pine, fir, spruce, and hemlock. It is preferred that the wood employed in the present invention be a wood part. In the context of the present invention the term "wood part" relates to any wooden article that used in construction, particularly those articles that are subject to outdoor exposure (such as decking, facia boards, exterior grade plywood, construction elements for outdoor furniture or playground equipment, fencing, and the like).

Boron-containing components suitable for use in the present invention include, but are not limited to, boric acid, boric oxide, diboron tetrahydroxide, borane, ammonium borate, and alkali metal borates such as sodium borate, sodium metaborate, sodium tetraborate and disodium octaborate. Organic boron compound can also be used for the present invention. Examples of organic boron compound are, but not limited to, (2-methyl-2,4-pentanediol)monoborate, triethanediol diborate, tri-(2,3-dimethyl-2,3-butanediol)diborate, tri-(2,5-dimethyl-2,5-hexanediol)diborate, tri-(2,6-dimethyl-4-heptanol)borate, triethanolamine borate and tri-isopropanolamine borate.

As used herein the term "biocidally effective" means the minimum amount of borate necessary to kill the targeted insects or soil microbes. A boron level of approximately 350 ppm is required to provide wood with resistance to fungus and common subterranean termites. For resistance against Formosan termites, a minimum of 700 ppm of boron is required. It is well within the ability of those skilled in the art to utilize the method of the present disclosure to produce wood that is impregnated with a desired biocidal level of borate.

In the methods of the present disclosure, it is preferred that the wood be immersed in the liquid containing boron-containing component and pH-reduced black liquor at an ambient temperature. Common solvents known in arts such as toluene can be used as the liquid medium, but an aqueous medium is most preferred. The liquid containing boron-containing component can be either a solution obtained from dissolving boron components directly into an aqueous phase, or an emulsion or dispersion obtained from homogenizing an aqueous phase and an oil phase with an emulsifier.

Where desired, the method of the present disclosure may be practiced at a neutral pH in the range of about 6.0 to about 10.0 to minimize potential corrosion problems with fasteners (such as nails, screws, and the like). However, with the advent of fasteners formed of plastic, stainless steel, and the like, this is less of a concern.

The impregnation of board with the wood preservative formulation of the present disclosure can be done by any method known to one of ordinary skill in the art including, but are not limited to, pressure treating, vacuum impregnating, soaking, spraying, painting, brushing, washing, dipping, rubbing, mixing, blending, infusion and the like. Furthermore, the impregnation of board can be carried out at atmospheric pressure, but it is more advantageously carried out at elevated pressure. "Loading" is a synonym for the absorption of the impregnating liquid dispersion or liquid solution by the wood and is—in the context of the present disclosure—also used for the respective technical impregnating process of immersing (and, preferably, applying pressure and subsequent relieving of the pressure). Methods of treating wood with chromated copper arsenate solutions and similar pesticidal mixtures at elevated pressures are well known in the art. The same equipment (e.g., pressure vessels) employed in such currently-used pesticide treatment methods can be readily adapted to the treatment of wood with the liquid of the present invention. Indeed, the wood may be immersed in any suitable vessel which can be closed to generate the given excess pressure for the loading. Likewise, pressures which are typically used for the production of chromated copper arsenate treated wood are suitable for use in the present method. A preferred pressure range is from about 50 psi to about 200 psi. After treating with borate preservative, the treated board is dried under ambient condition, although kiln drying or other heat treatment may be used to help fix the preservative components in the wood.

By way of example, a method of treating wood can include immersing wood in a liquid containing the boron containing compound and lignin, wherein the borate preservative level in the treating solution is from about 0.25% to 10% dry solids, and the weight ratio of lignin component to the borate-retaining component is from about 1:1 to 20:1; loading the immersed wood with the liquid under excess pressure for a period of time sufficient to impregnate the wood with a biocidally effective level of boron containing compound, thereafter relieving the excess pressure; and removing the wood from the liquid.

By way of another non-limiting example, a method of treating wood can include immersing wood in a liquid containing a boron containing compound and lignin; loading the immersed wood with the liquid under excess pressure; removing the wood from the liquid; air-drying the wood for at least one week; immersing the wood in the liquid containing a boron containing compound and lignin; loading the immersed wood with the liquid under excess pressure for a period of time sufficient to impregnate the wood with a biocidally effective level of the boron containing compound, thereafter relieving the excess pressure; and removing the wood from the liquid.

In some embodiments, a method of treating wood can include immersing wood in a liquid containing a boron containing compound; loading the immersed wood with the liquid under excess pressure; removing the wood from the liquid; air-drying the wood for at least one week; immersing the wood in a lignin containing liquid; loading the immersed wood with the lignin under excess pressure for a period of time sufficient to impregnate the wood, thereafter relieving the excess pressure; and removing the wood from the liquid.

In still other embodiments, a method of treating wood can include immersing wood in a liquid containing a lignin; loading the immersed wood with the liquid under excess pressure; removing the wood from the liquid; air-drying the wood for at least one week; immersing the wood in a boron containing compound; loading the immersed wood with the a boron containing compound under excess pressure for a period of time sufficient to impregnate the wood, thereafter relieving the excess pressure; and removing the wood from the liquid.

The upper limit of the applicable pressure mainly depends on the respective pressure needed to push the treating fluid into the interstitial void volumes within the wood matrix. This varies mainly with the wood being treated, some species being easier to impregnate than others, and the level of treating fluid that needs to impregnate the wood. In one embodiment, the applied pressure is in the range of about 20 psi to about 200 psi. Where desired, a vacuum may be applied to support the efficiency of the loading.

Pesticidal wood treatments currently in use, such as CCA and ACQ, impart a color to the wood due to the nature of the metal ions present. This color also serves as a convenient indication for the consumer that the wood has been so treated. Where desired, at least one dye and/or pigment can be added to the liquid dispersions and liquid solutions of the present invention in order to impart a color to the resulting wood to serve as a similar indicator. A combination of lignin and a green pigment such as chlorinated copper phthalocyanine is particularly effective in mimicking the color of CCA-treated wood. The use of light-fugitive dyes may be particularly advantageous in this application; as the use of such dyes permits the wood to be colored for identification but, once the wood is in place in or on an outdoor structure, the exposure to sunlight will bleach the dye and the wood will revert to its natural color.

Other additives including but not limited to surfactants, viscosity modifiers, dyes, pigments, water repellants, and the like may be included.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A wood preservative composition, comprising:
   a boron containing compound; and
   a pH-reduced black liquor comprising soluble lignin, wherein the boron containing compound is soluble in the pH-reduced black liquor and wherein the pH-reduced black liquor is derived from a carbonation process and/or an acid addition process of black liquor having phase separated solid lignin and/or dense liquid lignin removed therefrom.

2. The wood preservative composition of claim 1, wherein the pH-reduced black liquor has a pH within a range of less than about 13 to about 9 to 10.

3. The wood preservative composition of claim 1, wherein the pH-reduced black liquor is subjected to membrane filtration to remove a permeate comprising low molecular weight lignin having molecular weights between 200 and 2000 Daltons, organic salts, and/or inorganic salts.

4. The wood preservative composition of claim 1, wherein the pH-reduced black liquor is subjected to an oxygenation process to oxidize odorous compounds therein.

5. The wood preservative composition of claim 1, wherein the composition is an aqueous solution.

6. The wood preservative composition of claim 1, wherein the pH-reduced black liquor is oxygenated pH-reduced black liquor including a lower amount of odor causing compounds relative to pH-reduced black liquor that is not oxygenated.

7. Treated wood comprising:
   wood;
   at least one boron-containing component, and
   pH-reduced black liquor comprising soluble lignin, wherein the boron containing compound is soluble in the pH-reduced black liquor and wherein the pH-reduced black liquor is derived from a carbonation process and/or an acid addition process of black liquor having phase-separated solid lignin and/or dense liquid lignin removed therefrom.

8. The treated wood of claim 7, wherein at least one boron-containing component was from about 0.5% to 10% dry solids of the board weight.

9. The treated wood of claim 7, wherein a dry weight ratio of the boron-containing component to the pH-reduced black liquor was from about 1:1 to about 1:20.

10. The treated wood of claim 7, wherein the boron-containing component is selected from the group consisting of organic boron compound, boric acid, boric oxide, ammonium borate, alkali metal borate, diboron tetrahydroxide, metaborate, tetraborate, octaborate, pyroborate, borane, and mixture thereof.

11. The treated wood of claim 10 wherein the organic boron compound is a borate ester.

12. The treated wood of claim 11, wherein the borate ester is selected from the group consisting of (2-methyl-2,4-pentanediol)monoborate, bis-(2-aminoethyl)borate, tri-ethanediol diborate, tri-(2,3-dimethyl-2,3-butanediol)diborate, tri-(2,5-dimethyl-2,5-hexanediol)diborate, tri-(2,6-dimethyl-4-heptanol)borate, triethanolamine borate, tri-isopropanolamine borate, and mixtures thereof.

13. The treated wood of claim 10, wherein the alkali metal borate is selected from the group consisting of sodium borate, sodium metaborate, sodium tetraborate and disodium octaborate, and their hydrates and mixtures thereof.

14. The treated wood of claim 7, further comprising at least one member selected from the group consisting of dyes, pigments, surfactants, viscosity modifiers, water repellants and mixture thereof.

15. The treated wood of claim 7, wherein the wood is selected from the group consisting of pine, fir, spruce, hemlock oak, maple, poplar, teak and combinations thereof.

16. The treated wood of claim 7, wherein the pH-reduced black liquor has a pH within a range of less than about 13 to about 9 to 10.

17. A method for treating wood, comprising:
   applying to the wood, a wood preservative formulation comprising a boron containing compound, and pH-reduced black liquor comprising soluble lignin, wherein the boron containing compound is soluble in the pH-reduced black liquor and wherein the pH-reduced black liquor is derived from a carbonation process or an acid addition process of black liquor having phase-separated solid lignin and/or dense liquid lignin removed therefrom.

18. The method of treating wood of claim 17, further comprising drying the wood.

19. The method for treating wood of claim 17, wherein the boron-containing component is selected from the group consisting of organic boron compound, boric acid, boric oxide, ammonium borate, alkali metal borate, diboron tetrahydroxide, metaborate, tetraborate, octaborate, pyroborate, borane, and mixture thereof.

20. The method for treating wood of claim 17, wherein the organic boron compound is selected from the group consisting of (2-methyl-2,4-pentanediol)monoborate, bis-(2-aminoethyl)borate, triethanediol diborate, tri-(2,3-dimethyl-2,3-butanediol)diborate, tri-(2,5-dimethyl-2,5-hexanediol) diborate, tri-(2,6-dimethyl-4-heptanol)borate, triethanolamine borate, tri-isopropanolamine borate, and mixture thereof.

21. The method for treating wood of claim 17, wherein the alkali metal borate is selected from the group consisting of sodium borate, sodium metaborate, sodium tetraborate and disodium octaborate, and their hydrates and mixture thereof.

22. The method for treating wood of claim 17, wherein applying the wood preservative formulation comprises pressure treating, vacuum impregnating, soaking, spraying, painting, brushing, washing, dipping, rubbing, mixing, blending, infusion or a combination thereof.

23. The method of claim 17, wherein the pH-reduced black liquor has a pH within a range of less than about 13 to about 9 to 10.

24. A method for treating wood, comprising:
applying a boron containing compound to the wood; and
applying a pH-reduced black liquor to the wood, wherein the pH-reduced black liquor comprises soluble lignin, wherein the boron containing compound is soluble in the pH-reduced black liquor, and wherein the pH-reduced black liquor is derived from a carbonation process or an acid addition process of black liquor having phase-separated solid lignin and/or dense liquid lignin removed therefrom.

25. The method of claim 24, further comprising drying the wood.

26. The method of claim 24, wherein applying the pH-reduced black liquor is prior to applying the boron containing compound to the wood.

27. The method of claim 24, wherein applying the boron containing compound and the pH-reduced black liquor comprises forming a mixture of the boron containing compound and the pH-reduced black liquor, and applying the mixture to the wood.

28. The method of claim 24, further comprising membrane filtering the pH-reduced black liquor to remove salts and lower molecular weight lignin.

29. The method of claim 24, further comprising oxygenating the pH-reduced black liquor to reduce odorous compounds therein prior to applying to the wood.

30. The method of claim 24, wherein oxygenating the pH-reduced black liquor comprises applying a high shear cavitation process to the pH-reduced black liquor for a period of time effective to reduce the odorous compounds therein.

31. The method of claim 24, wherein the pH-reduced black liquor has a pH within a range of less than about 13 to about 9 to 10.

* * * * *